United States Patent [19]

Sandrin et al.

[11] 4,291,022
[45] Sep. 22, 1981

[54] ORGANIC COMPOUNDS

[75] Inventors: Edmond Sandrin, Riehen; Wilfried Bauer, Lampenberg, both of Switzerland

[73] Assignee: Sandoz Ltd., Basel, Switzerland

[21] Appl. No.: 152,706

[22] Filed: May 23, 1980

Related U.S. Application Data

[63] Continuation-in-part of Ser. No. 84,661, Oct. 15, 1979, which is a continuation of Ser. No. 915,181, Jun. 14, 1978, abandoned, which is a continuation of Ser. No. 829,855, Sep. 10, 1977, abandoned, which is a continuation-in-part of Ser. No. 663,824, Mar. 4, 1976, abandoned.

[30] Foreign Application Priority Data

| | | | |
|---|---|---|---|
| Mar. 11, 1975 | [CH] | Switzerland | 3055/75 |
| Mar. 20, 1975 | [CH] | Switzerland | 3572/75 |
| Aug. 14, 1975 | [CH] | Switzerland | 10610/75 |
| Sep. 22, 1975 | [CH] | Switzerland | 12282/75 |
| Sep. 29, 1975 | [CH] | Switzerland | 12586/75 |
| Nov. 21, 1975 | [CH] | Switzerland | 15117/75 |
| Nov. 21, 1975 | [CH] | Switzerland | 15118/75 |
| Nov. 21, 1975 | [CH] | Switzerland | 15119/75 |
| Nov. 25, 1975 | [CH] | Switzerland | 15252/75 |

[51] Int. Cl.³ .................. A61K 37/00; C07C 103/52
[52] U.S. Cl. .................. 424/177; 260/112.5S
[58] Field of Search .................. 260/112.5 S; 424/177

[56] References Cited

U.S. PATENT DOCUMENTS 4,120,852  10/1978  Bauer et al. .................. 260/112.5 S

*Primary Examiner*—Delbert R. Phillips
*Attorney, Agent, or Firm*—Gerald D. Sharkin; Robert S. Honor

[57] ABSTRACT

This invention provides new compounds of formula I,

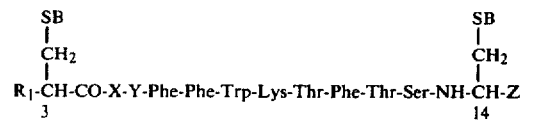

wherein
$R_1$, X, Y and Z are amino acid residues and
each B is hyrogen or together are a bond, useful as growth hormone secretion inhibitors.

7 Claims, No Drawings

ORGANIC COMPOUNDS

This is a continuation-in-part of our co-pending application Ser. No. 084,661 filed Oct. 15th, 1979, which in turn is a continuation of our application Ser. No. 915,181 filed June 14th, 1978, now abandoned, which in turn was a continuation of our application Ser. No. 829,855 filed Sept. 10, 1977, now abandoned, which in turn was a continuation-in-part of our application Ser. No. 663,824 filed Mar. 4th, 1976, now abandoned.

The present invention relates to new polypeptides.

In accordance with the invention there are provided new compounds of formula I,

```
       SB                              SB
       |                               |
       CH2                             CH2
       |                               |
   R1-CH-CO-X-Y-Phe-Phe-Trp-Lys-Thr-Phe-Thr-Ser-NH-CH-Z     I
       3                                          14
``` wherein $R_1$ is
(i) H,
(ii) $NH_2$,
(iii)
   H—Ala—NH—;
   H—Tyr—NH—;
   H—Cys—NH—;
   H—Val—NH—;
   H—Lys—NH—;
   H—(α-amino-isobutyryl)—NH—;
   H—Phe—NH—;
(iv) $NH_2$—NH—CO—NH—;
(v)
   $C_6H_5$.NH—CO—Gly—NH—;
   H—Ala—Gly—NH—;
   H—Val—Gly—NH—;
   H—α—phenyl—Gly—NH—;
(vi) $R_2$—A—CO—NH—,
   wherein
   $R_2$ is lower alkyl, phenyl, or phenyl substituted by halogen, hydroxy, amino, lower alkyl or lower alkoxy,
   A is a direct bond, alkylene containing up to 6 carbon atoms or —NH—,
(vii)
   $R_2$—Ala—NH—;
   $R_2$—Ala—Gly—NH—;
   wherein $R_2$ is as defined above,
(viii)
   $C_6H_5.A^I$.CO—M—NH—,
   wherein
   $A^I$ is an alkylene chain of up to 6 carbon atoms, and —M— is —(mono- di-Hal)—Phe, —Gly— or —Ala—,
(ix) T—(mono- or di-Hal)—Phe—NH—,
   wherein
   T— is H—, H—Val— or benzoyl—,
(x)

$$(CH_2)_n CH . A^I . CO—L—NH,$$

wherein
   $A^I$ is as defined above, and
   —L— is —Val—, —Val—(mono- or di-Hal-)—Phe—, —α—phenyl—Gly—,
   and n is an integer between 4 and 10, each B is hydrogen or the two radicals β form a direct bond,
X is —Lys—, —Nle— or —Cys—, and
Y is —Asn—, —Gln— or —Thr—, and
Z signifies the radicals (i) H; (ii) COOH, (iii) $COOR_3$ (wherein $R_3$ is lower alkyl); (iv) —CO—$NR_4R_5$ (wherein $R_4$ and $R_5$ independently are hydrogen or lower alkyl); (V)

$$—CON\overbrace{(CH_2)_n}$$

(wherein n is as defined above); (vi) $CH_2OH$; (vii) —CO—asparaginol; —CO—leucinol; —CO—isoleucinol; —CO—valinol; —CO—norleucinol; —CO—glutaminol; —CO—threoninol; (viii) —CO—Leu; —CO—Ser; —CO—Iso-Leu; —CO—Val, and their corresponding amides, wherein the amide portion signifies the radical —CO—$NR_4R_5$ or $$—CO—N(CH_2)_n$$

(wherein n, $R_4$ and $R_5$ are as defined above), or (ix) —CO—$ThrOR_3$ or —CO—$SerOR_3$ (wherein $R_3$ is as defined above); (x) —CO—NH—$(CH_2)_k$—OH (wherein k is an integer between 2 and 6), of $$—CO—NH—CH—[CH_2]_{l_1}OH$$
$$\phantom{—CO—NH—CH—}[CH_2]_{l_2}OH$$

wherein $l_1$ and $l_2$ independently signify a whole number from 1 to 6); (xi)

$$—CO—N\diagup\diagdown O;$$

(xii) —CO—NH—$R_6$ (wherein $R_6$ is a 5- or 6-membered saturated heterocyclic ring having an oxygen atom as sole hetero atom, or a 5- or 6-membered lactone ring), wherein in formula I the unit containing radicals $R_1$, X, Y and Z, as well as in the remaining units of the peptide sequence, at least one unit may be present in D form, with the provisos that when X is Lys and Y is Asn, and all the remaining units of the peptide sequence 3 to 14 are present in the D or L form, and when
(i)
   $R_1$ is H—Ala—Gly—NH— or H—(D)—Ala—Gly—NH—
   Z is other than COOH, $COOR_3$, $CH_2OH$ or $CONR_4R_5$, or, when
(ii)
   $R_1$ is H, $NH_2$ or H—(D)—Ala—Gly—NH—,
   Z is other than H, COOH, $CONR_4R_5$ or $$CON\overbrace{(CH_2)_4}$$

or 5, or, when (iii) $R_1$ is H—(α-amino-isobutyryl)—NH— or H—(D-)—Ala—NH—,

Z is other than H or COOH, or, when (iv) $R_1$ is H—Ala—Gly—NH—,

Z is other than H, or, when (v) $R_1$ is H—Ala—NH— or $R_2'$—CO—NH— (wherein $R_2'$ is lower alkyl or unsubstituted phenyl), Z is other than COOH, and with the further proviso that when $R_1$ is H—Cys—NH or H—(D)—Cys—NH and/or X is —Cys— or —(D-)—Cys, B-B is other than a direct bond.

Halogen signifies bromine, fluorine, and preferably chlorine. The significance of lower alkyl or lower alkoxy comprises up to 6 carbon atoms, but preferably signifies 2 or 1 carbon atom.

When $R_6$ is substituted phenyl, this is preferably mono- or disubstituted, especially, however, monosubstituted. A substituent is preferably present in the para position.

A when alkylene or $A^I$ preferably contains up to 3 carbon atoms. In regard to the significance (viii), $A^I$ preferably signifies trimethylene. In regard to the significance (x), $A^I$ preferably signifies methylene.

Examples of —(mono- or di-Hal)—Phe— moieties are —(2Cl)—Phe—; —(3Cl)—Phe—; —(4Cl)—Phe— or —(3,4-di-Cl)—Phe—.

n preferably signifies an integer 5 or 4.

$R_1$ preferably signifies, e.g., H—(mono- or di-Hal)—Phe—NH—, phenyl—CO—NH—, H—Val—(mono- or di-Hal)—Phe—NH—, phenylbutyryl—NH— or a radical containing —(D-)—Ala, benzoyl—(mono- or di-Hal)—Phe—NH—, cyclohexylacetyl—α—phenyl—Gly—NH—, cyclohexylacetyl—Val—(mono- or di-Hal)—Phe—NH—, cyclohexylacetyl—Val—NH—, H—Val—NH, H, H—(α-aminoisobutyryl-)—NH—, H—(mono- or di-Hal)—Phe—NH—.

X preferably signifies Lys and especially Nle.
Y preferably signifies Gln and especially Asn.
k preferably signifies 2 or 3.

When Z is significance (x) or (xii), this preferably contains a moiety

and signifies, for example, —CO.NH.CH(CH$_2$.OH)CH$_2$.CH$_2$.CH$_2$.OH; —CO—NH—CH(CH$_2$OH).CH$_2$.CH$_2$.OH;

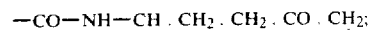

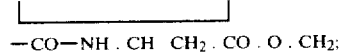

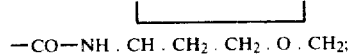

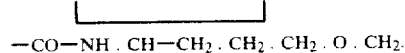

Z preferably signifies other than H, CH$_2$OH, COOH or COOR$_3$.

In the preferred significance indicated above the aminoacids may be present in the D instead of the L form.

The present invention comprises processes for the production of compounds of the above formula. They may be produced in accordance with known methods for the synthesis of compounds of this type or obvious chemical equivalents thereof.

The polypeptides or derivatives thereof of the above formula may be produced, for example, by a process comprising (a) removing at least one protective group from a protected peptide having the sequence indicated in formula I, or (b) linking together by an amide bond two peptide units, each of which contains at least one aminoacid and which is in protected or unprotected form, the peptide units being such that the aminoacid sequence given in formula I is obtained, and then if necessary carrying out process step (a), or (c) converting one group Z of an unprotected or protected peptide of formula I into another group Z having the definition indicated above, and if necessary carrying out process (a), or (d) oxidizing a peptide of formula I wherein B is hydrogen, to produce a peptide of formula I wherein B-B is a direct bond.

The above are methods known in peptide chemistry; they may be carried out in a manner analogous to the processes described in the following Examples.

Insofar as the production of the starting materials is not particularly described, these compounds are known or may be produced and purified in accordance with known methods. These compounds may also be produced in a manner analogous to the processes described in the Examples.

The compounds may exist in salt form or in the form of complexes thereof.

The salts of hydrochloric acid and acetic acid may particularly be mentioned as acid addition salts.

Complexes are understood to be the complex-like compounds of known type, but not of clear structure, which are formed from compounds of formula I upon adding certain inorganic or organic substances. Such inorganic substances are compounds which are derived from metals, such as calcium, magnesium, aluminium, cobalt and particularly zinc, especially difficulty soluble salts such as phosphates, pyrophosphates and polyphosphates, as well as hydroxides of these metals, in addition alkali metal polyphosphates. Organic substances are, for example, non-antigenic gelatines, e.g. oxypolygelatine, polyvinylpyrrolidone and carboxymethyl cellulose, in addition sulphonic acid or phosphoric acid esters of alginic acid, dextrane, polyphenols and polyalcohols, especially polyphloretine phosphate and phytinic acid, as well as polymerization products of aminoacids, e.g. protamine, polyglutaminic acid or polyasparaginic acid.

In the following non-limitative Examples all temperatures are indicated in degrees centigrade and are uncorrected.

The following abbreviations are used:
Cbo = carbobenzyloxy
MBzl = p-methoxybenzyl
Iabu = H—(α-amino-isobutyryl)—
(4Cl)Phe = p-chlorophenylalanyl
AcOH = acetic acid
OCP = trichlorophenyl ester
OSu = O-succinimide Asp-diol = Aspanaginediol = L-2-Aminobutane-1,4-diol
BOC = tert.butoxycarbonyl
MBzl = p-methoxybenzyl
Me = methyl
ONP = p-nitrophenoxy
Z = benzyloxycarbonyl All the final compounds are characterized in hydrochloride salt form. The aminoacids are present in the L form unless otherwise indicated.

In the following Table $[\alpha]_D^{20}$ refers to AcOH 1% v/v (c = 1) unless otherwise indicated.

(1) refers to AcOH 20% v/v (c = 1)
(2) refers to AcOH 1% v/v (c = 0.25)
(3) refers to AcOH 30% v/v (c = 1)
(4) refers to AcOH 40% v/v (c = 1)
(5) refers to AcOH 50% v/v (c = 1)

EXAMPLE 1

H-(4Cl)Phe-Cys-Lys-Asn-Phe-Phe-Trp-Lys-Thr-Phe-Thr-Ser-Cys-OH 480 mg of Cbo-(4Cl)Phe-Cys(MBzl)-Lys(BOC)-Asn-Phe-Phe-Trp-Lys(Cbo)-Thr-Phe-Thr-Ser-Cys(MBzl)-OBzl, 410 mg of H-Try-OH, 320 mg of H-Cys-OH.HCl and 1,2 cc of thioanisole are dissolved at 0° in 5 cc of trifluoroacetic acid, and 10 cc of 2 molar boron tris(trifluoroacetate) in trifluoroacetic acid are added. The mixture is shaken for one hour at room temperature and cooled. 50 cc of tert.butyl alcohol are added, concentration is effected by evaporation in a vacuum and a solution of 0.01 molar 2-mercaptoethanol in ether is added to the residue. Centrifuging is subsequently effected. The solid residue is dissolved in a small amount of 10% acetic acid and is purified by chromatography on Sephadex G 25 in a system of 0.01 molar 2-mercaptoethanol in 10% acetic acid. The residue may also be dissolved in 30% acetic acid or in a mixture of n-butanol/acetic acid/water (e.g. 4:2:1), and purified by chromatography on Sephadex G 25 using 0.01 M 2-mercaptoethanol in 30% acetic acid or in the mixture of n-butanol/acetic acid/water. The fractions containing the desired product are combined, dissolved in 0.1 normal hydrochloric acid and lyophilized, whereby the title compound is obtained.

M.Pt. 195° (decomp.); $[\alpha]_D^{20} = -20.5°$ in AcOH (c = 1).

The starting material is produced as follows:

(a) Cbo-Lys(BOC)-Asn-Phe-OMe 74.8 g of Cbo-Lys(BOC)-ONP are reacted in a solution of 51 g of H-Asn-Phe-OMe.HCl and 21 cc of triethylamine in 300 cc of dimethyl formamide. After working up, the title compound is obtained.

M.P. 175°; $[\alpha]_D^{20} = -4.4°$ in dimethyl formamide (c = 1.0).

(b) H-Lys(BOC)-Asn-Phe-OMe 92 g of Cbo-Lys(BOC)-Asn-Phe-OMe are suspended in a solution of 2 liters of dioxane and 400 cc of water. Palladium charcoal is added and hydrogenation is effected at normal pressure. After working up, the title compound is obtained.

M.P. 122°; $[\alpha]_D^{20} = -8.3°$ in dimethyl formamide (c = 1.0).

(c) Cbo-(4Cl)Phe-Cys(MBzl)-NH-NH$_2$ 20 g of H-Cys(MBzl)-OMe.CH$_3$SO$_3$H and 7 cc of triethylamine are dissolved in 120 cc of dimethyl formamide, and 18.2 g of Cbo-(4Cl)Phe-ONP are added. The mixture is allowed to stand for 16 hours and is concentrated at room temperature, whereby Cbo-(4Cl)Phe-Cys(MBzl)-OMe (M.P. 115°) is obtained after working up. The latter is dissolved in methanol and hydrazine hydrate is added. The mixture is allowed to stand at room temperature for one day. The title compound is obtained after working up.

M.P. 158°; $[\alpha]_D^{20} = -9.9°$ in dimethyl formamide (c = 1).

(d) Cbo-(4Cl)Phe-Cys(MBzl)-Lys(BOC)-Asn-Phe-NH-NH$_2$ 6 g of Cbo-(4Cl)Phe-Cys(MBzl)-NH-NH$_2$ are dissolved in 80 cc of dimethyl formamide, the solution is cooled to −20°, 6 cc of 5.3 normal hydrochloric acid in dioxane are added and then 1.3 cc of tert.butyl nitrite are added and stirring is effected at −20° for 10 minutes. After the addition of 5.5 cc of triethylamine at −20°, 8.4 g of H-Lys(BOC)-Asn-Phe-OMe are added, the mixture is allowed to stand over night at 0°, concentration is effected, and water is added at 0° up to pH 2. The precipitate is filtered off and washed with water. The resulting Cbo-(4Cl)Phe-Cys(MBzl)-Lys(Boc)-Asn-Phe-OMe is recrystallized from methanol, is then dissolved in dimethyl formamide, and 7 cc of hydrazine hydrate are added. The mixture is allowed to stand at room temperature for one day, is concentrated, and the residue is recrystallized from methanol, whereby the title compound is obtained. M.P. 260°; $[\alpha]_D^{20} = -23°$ in dimethyl formamide (c = 1.0).

(e) BOC-Lys(Cbo)-Thr-Phe-Thr-Ser-Cys(MBzl)-OBzl 2.3 g of BOC-Lys(Cbo)-Thr-Phe-Thr-Ser-NH-NH$_2$ are reacted with 1.86 g of H-Cys(MBzl)-OBzl in a manner analogous to that described in section (d), whereby the title compound is obtained.

M.P. 169°; $[\alpha]_D^{20} = -16°$ in dimethyl formamide (c = 1).

(f) BOC-Trp-Lys(Cbo)-Thr-Phe-Thr-Ser-Cys(MBzl)-OBzl 2.3 g of BOC-Lys(Cbo)-Thr-Phe-Thr-Ser-Cys(MBzl)-OBzl are dissolved in a mixture of 10 cc of methylene chloride and 6 cc of trifluoroacetic acid and the solution is allowed to stand at room temperature for 25 minutes. H-Lys(Cbo)-Thr-Phe-Thr-Ser-Cys(MBzl)-OBzl.trifluoroacetate is subsequently precipitated with ether, filtered off and washed out well with ether. The residue is dissolved in 7 cc of dimethyl formamide, 1.5 g of BOC-Trp-OCP and 0.3 cc of triethylamine are added and the mixture is allowed to stand at room temperature over night. The product is precipitated with ether/ethyl acetate (1:1) and is filtered. Drying is effected, whereby the tilte compound is obtained.

M.P. 167°; $[\alpha]_D^{20} = -17.5°$ in dimethyl formamide (c = 1).

(g) BOC-Phe-Trp-Lys(Cbo)-Thr-Phe-Thr-Ser-Cys(MBzl)-OBzl 36 g of BOC-Trp-Lys(Cbo)-Thr-Phe-Thr-Ser-Cys(MBzl)-OBzl are reacted with 20 g of BOC-Phe-ONP in a manner analogous to that described in section (f); the title compound is obtained.

M.P. 210°; $[\alpha]_D^{20} = 15°$ in dimethyl formamide (c = 1.0).

(h)
Cbo-(4Cl)Phe-Cys(MBzl)-Lys(BOC)-Asn-Phe-Phe-Trp-Lys(Cbo)-Thr-Phe-Thr-Ser-Cys(MBzl)-OBzl 1.5 g of BOC-Phe-Trp-Lys(Cbo)-Thr-Phe-Thr-Ser-Cys(MBzl)-OBzl are dissolved in 30 cc of methylene chloride and 30 cc of trifluoroacetic acid. The mixture is allowed to stand at room temperature for 25 minutes, is concentrated by evaporation in a vacuum and precipitated with ether. After filtration, washing with ether and drying, H-Phe-Trp-Lys(Cbo)-Thr-Phe-Thr-Ser-Cys(MBzl)-OBzl. trifluoroacetate is obtained.

0.9 g of Cbo-(4Cl)Phe-Cys(MBzl)-Lys(BOC)-Asn-Phe-NH-NH$_2$ are dissolved in 20 cc of dimethyl formamide, the solution is cooled to −20°, 0.6 cc of 5.3 normal hydrochloric acid in dioxane are added and then 0.1 cc of tert.butyl nitrite is added and the mixture is stirred at −20° for 15 minutes. 0.7 cc of triethylamine and 1.5 g of H-Phe-Trp-Lys(Cbo)-Thr-Phe-Thr-Ser-Cys(MBzl)-OBzl. trifluoroacetate are added. The mixture is allowed to stand at 0° over night, is concentrated by evaporation in a vacuum, is stirred with 100 cc of water, filtration is effected, the residue is washed with water and then with methanol, heating in methanol and filtration are effected, whereby the title compound is obtained. M.P. 270°; $[\alpha]_D^{20} = −19.3°$ in dimethyl formamide (c = 1).

The following compounds of formula A are obtained in analogous manner after building up the corresponding protected compounds and splitting off the protective group, P-Phe-Phe-Trp-Lys-Thr-Phe-Thr-Ser-Q    A

| Ex. No. | P | Q | M.P./$[\alpha]_D^{20}$ |
|---|---|---|---|
| A1 | ⟨phenyl⟩—NH—CO—Cys—Lys—Asn | Cys—OH | 160°/ −17.2° |
| A2 | ⟨phenyl⟩—NH—CO—Cys—Lys—Gln | Cys—OH | 150°/ −24.6° |
| A3 | H—Tyr—Cys—Lys—Asn | Cys—OH | 160°/ −20.0° |
| A4 | NH$_2$—⟨phenyl⟩—CO—Cys—Lys—Asn | Cys—OH | 170°/ −19.8° |
| A5 | ⟨phenyl⟩—(CH$_2$)$_3$—CO—Cys—Lys—Asn | Cys—OH | 160°/ −33.1° |
| A6 | ⟨phenyl⟩—(CH$_2$)$_3$—CO—Gly—Cys—Lys—Asn | Cys—OH | 170°/ −27.7° |
| A7 | ⟨phenyl⟩—NH—CO—Gly—Cys—Lys—Asn | Cys—OH | 160°/ −34.3° |
| A8 | H—Cys—Cys—Lys—Asn | Cys—NH$_2$ | 160°/ −24.5° |
| A9 | H—Cys—Cys—Asn | Cys—NH$_2$ | 170°/ −23.3° |
| A10 | H—Lys—Cys—Lys—Asn | Cys—NH$_2$ | 175°/ −27.8° |
| A11 | H—(4Cl)Phe—Cys—Nle—Asn | Cys—NH$_2$ | 170°/ −22.4° |
| A12 | H—(4Cl)Phe—Cys—Lys—Asn | Cys—NH$_2$ | 175°/ −23.2° |
| A13 | H—Iabu—Cys—Lys—Asn | Cys—NH$_2$ | 165°/ −21.0° |
| A14 | H—Iabu—Cys—Lys—Thr | Cys—NH$_2$ | 165°/ −20.2° |
| A15 | ⟨phenyl⟩—(CH$_2$)$_3$—CO—(4Cl)Phe—Cys—Lys—Asn | Cys—NH$_2$ | 160°/ −18.7° |
| A16 | ⟨phenyl⟩—(CH$_2$)$_3$—CO—Gly—Cys—Nle—Gln | Cys—NH$_2$ | 155°/ −18.7° |
| A17 | ⟨phenyl⟩—(CH$_2$)$_3$—CO—Cys—Lys—Asn | Cys—NH$_2$ | 145°/ −19.5° |
| A18 | ⟨phenyl⟩—NH—CO—Cys—Lys—Asn | Cys—NH$_2$ | 160°/ −25.3°(1) |
| A19 | ⟨phenyl⟩—NH—CO—Cys—Lys—Gln | Cys—NH$_2$ | 135°/ −29.5° |
| A20 | ⟨phenyl⟩—NH—CO—Cys—Nle—Asn | Cys—NH$_2$ | 145°/ −10.7° |
| A21 | ⟨phenyl⟩—NH—CO—Gly—Cys—Nle—Gln | Cys—NH$_2$ | 150°/ −13.4° |
| A22 | NH$_2$—NH—CO—Cys—Lys—Asn | Cys—NH$_2$ | 130°/ |

-continued

| Ex. No. | P | Q | M.P./$[\alpha]_D^{20}$ |
|---|---|---|---|
| A23 | ⌬—(CH$_2$)$_3$—CO—(D)Ala—Cys—Lys— | Cys—NH$_2$ | −15.8°<br>140°/<br>−13.7° |
| A24 | Benzoyl-Cys—Nle—Asn | Cys—NH$_2$ | 160°/<br>−34.4° |
| A25 | Benzoyl-Cys—Lys—Asn | Cys—NH$_2$ | 155°/<br>−37.9° |
| A26 | ⌬—CO—(4Cl)Phe—Cys—Nle—Asn | Cys—NH$_2$ |  |
| A27 | H—(D)-Ala—Gly—Cys—Lys—Asn | Cys—Val—NH$_2$ | 220°/<br>−47°(2) |
| A28 | H—Ala—Gly—Cys—Lys—Asn | Cys—N⌬ | 210°/<br>−45°(2) |
| A29 | H—(4Cl)Phe—Cys—Nle—Asn | Cys—Asparaginol | 155°/<br>−22.5° |
| A30 | H—Iabu—Cys—Nle—Asn | Cys—Asparaginol | 150°/<br>−44.3° |
| A31 | H—Iabu—Cys—Lys—Asn | Cys—Asparaginol | 160°/<br>−47.4° |
| A32 | H—(D)-Ala—Gly—Cys—Lys—Asn | Cys—Asparaginol | 150°/<br>−52.7° |
| A33 | H—(D)-Ala—Gly—Cys—Nle—Asn | Cys—Asparaginol | 165°/<br>−49.5°(1) |
| A34 | H—(D)-Val—Cys—Lys—Asn | Cys—NH$_2$ | 175°/<br>−47.0° |
| A35 | H—(α-Phenylglycyl)-Cys—Lys—Asn | Cys—NH$_2$ | 180°/<br>−33.3° |
| A36 | H—(D)-Val—(4Cl)Phe—Cys—Lys—Asn | Cys—NH$_2$ | 165°/<br>−30.9° |
| A37 | H—(D)-Ala—Cys—Lys—Asn | Cys—NH$_2$ |  |
| A38 | H—Cys—Lys—Asn | Cys—NH$_2$ | 180°/<br>−27.5° |
| A39 | Cyclohexylacetyl-(D)-Val—Cys—Lys—Asn | Cys—NH$_2$ | 160°/<br>−19.8°(3) |
| A40 | Cyclohexylacetyl-(α-Phenyl-glycyl)-Cys—Lys—Asn | Cys—NH$_2$ | 165°/<br>−19.6°(5) |
| A41 | Cyclohexylacetyl-(D)-Val—(4Cl)Phe—Cys—Lys—Asn | Cys—NH$_2$ | 165°/<br>−23.7°(3) |
| A42 | Benzoyl-(3,4-dichloro)Phe—Cys—Lys—Asn | Cys—NH$_2$ | 180°/<br>−22.5°(4) |
| A43 | Benzoyl-(3,4-dichloro)Phe—Cys—Nle—Asn | Cys—NH$_2$ | 175°/<br>−23.5°(4) |
| A44 | H—(D)-Ala—Gly—Cys—Nle—Asn | Cys—NH$_2$ | 160°/<br>−23.9°(4) |
| A45 | H—(D)-Phe—Cys—Nle—Asn | Cys—NH$_2$ | 175°/<br>−29.1°(3) |
| A46 | H—Phe—Cys—Nle—Asn | Cys—NH$_2$ | 170°/<br>−30.8°(3) |
| A47 | H—(3Cl)Phe—Cys—Nle—Asn | Cys—Asparaginol | 165°/<br>−35.0°(3) |
| A48 | H—(2Cl)Phe—Cys—Nle—Asn | Cys—Asparaginol | 170°/<br>−29.8°(3) |
| A49 | H—(3,4diCl)Phe—Cys—Nle—Asn | Cys—Asparaginol | 162°/<br>−25.5°(3) |
| A50 | H—(4Cl)Phe—Cys—Nle—Asn | Cys—NH—CH(CH$_2$—C=O / O / CH$_2$) | 165°/<br>−17.8°(3) |

EXAMPLE 2

H—(D)—Ala—Gly—Cys—Nle—Asn—Phe—Phe—Trp—Lys—Thr—Phe—Thr—Ser—Cys—asparaginol 0.4 g of the compound of Example A33 is dissolved in a mixture of methanol and 0.5% acetic acid, and the pH is adjusted to 6–7 by the addition of ammonium hydroxide solution with stirring. A 0.1 molar potassium ferricyanide solution is slowly added with stirring until the yellow colouration remains. After stirring for a further 15 minutes, the pH is adjusted to 4–5 with acetic acid. Filtration is effected through a short column of Bio Rad AG 3/x4 (Cl⊖ form) [≐slightly basic anion exchange resin]. The filtrate is then allowed to flow slowly at 0° through a column with Bio Rex 70 (—COOH form) [≐slightly acid cation exchange resin]. The column is then eluted with an acetic acid gradient with increasing concentrations of acetic acid or with an acetic acid/pyridine gradient. The fractions containing the desired product are combined and lyophilized. The lyophilization product is dissolved in a small amount of n-butanol/glacial acetic acid/water (2:1:1) or 30% acetic acid and purified by chromatography on Sephadex G 25 in the same mixture. The fractions containing the desired product are combined and lyophilized, whereby the title compound is obtained. $[\alpha]_D^{20} = -36°$ (c=1 in 95% acetic acid).

The corresponding compounds having an S-S-bridge are produced in analogous manner from the corresponding compounds having a free SH function (Examples 1, A 1–7, A 10–32, A 34–50).

In analogous manner to that described in Example 1 the following compounds of formula A are produced, wherein:

| | P | Q |
|---|---|---|
| (i) | | |
| A51 | H—(4Cl)Phe—Cys—Nle—Asn | Cys—NH—[CH$_2$]$_2$—OH |
| A52 | H—(4Cl)Phe—Cys—Nle—Asn | Cys—NH—[CH$_2$]$_3$—OH |
| A53 | H—(4Cl)Phe—Cys—Nle—Asn | Cys—Threoninol |
| A54 | H—(4Cl)Phe—Cys—Nle—Asn | Cys—Thr—O—CH$_3$ |
| A55 | H—(4Cl)Phe—Cys—Nle—Asn | Cys—Ser—O—CH$_3$ |
| A56 | H—(4Cl)Phe—Cys—Nle—Asn | Cys—Ser—NH$_2$ |
| A57 | H—(4Cl)Phe—Cys—Nle—Asn | Cys—NH—CH(CH$_2$OH)—CH$_2$OH |
| A58 | H—(4Cl)Phe—Cys—Nle—Asn | Cys—Glutaminol |
| A59 | H—(4Cl)Phe—Cys—Nle—Asn | Cys—NH—CH(CH$_2$—CH$_2$—OH)—CH$_2$—OH |
| A60 | H—(4Cl)Phe—Cys—Nle—Asn | Cys—NH—CH(CH$_2$—CH$_2$—CH$_2$—OH)—CH$_2$—OH |
| A61 | H—(4Cl)Phe—Cys—Nle—Asn | Cys—NH—CH(—CH$_2$—CH$_2$—)(—CH$_2$—O—)C=O |
| (ii) | | |
| A62 | H—(D)—Phe—Cys—Nle—Asn | Cys—Asparaginol |
| A63 | H—(D)—Val—(4Cl)Phe—Cys—Nle—Asn | Cys—Asparaginol |
| A64 | H—(D)—Ala—(4Cl)Phe—Cys—Nle—Asn | Cys—Asparaginol |

The compounds are also converted into the corresponding ring closed forms. It will be appreciated that these ring closed forms may be characterized by reduction back into the open chain forms.

In analogous manner to Example 1 the following compounds of formula A may be made, wherein

| | P | Q |
|---|---|---|
| B1 | CH$_2$—SH \| CH$_2$—CO—Cys—Cys—Thr | Cys—OnBu |
| B2 | H—Val—Gly—Cys—Cys—Thr | Cys—Leucinol |
| B3 | nBu—Ala—Cys—Cys—Thr | Cys—IsoLeucinol |
| B4 | HO—C$_6$H$_4$—Ala—Gly—Cys—Cys—Thr | Cys—OnBu |
| B5 | Br—C$_6$H$_4$—Ala—Gly—Cys—Cys—Thr | Cys—N(nBu)$_2$ |
| B6 | NH$_2$—C$_6$H$_4$—Ala—Gly—Cys—Cys—Thr | Cys—Valinol |
| B7 | nBu—C$_6$H$_4$—Ala—Gly—Cys—Cys—Thr | Cys—NorLeucinol |
| B8 | nBuO—C$_6$H$_4$—Ala—Gly—Cys—Cys—Thr | Cys—Glutaminol |
| B9 | nBuO—C$_6$H$_4$—Ala—Gly—Cys—Cys—Thr | Cys—Leu |
| B10 | nBuO—C$_6$H$_4$—Ala—Gly—Cys—Cys—Thr | Cys—Ser |
| B11 | nBuO—C$_6$H$_4$—Ala—Gly—Cys—Cys—Thr | Cys—iso—Leu—CON(nBu)$_2$ |

-continued

| | P | Q |
|---|---|---|
| B12 | nBuO—⟨phenyl⟩—Ala—Gly—Cys—Cys—Thr | Cys—Val—N⟨ring⟩ |
| B13 | nBuO—⟨phenyl⟩—Ala—Gly—Cys—Cys—Thr | Cys—NH—[CH₂]₆OH |
| B14 | nBuO—⟨phenyl⟩—Ala—Gly—Cys—Cys—Thr | Cys—NH—[CH₂]OH |
| B15 | n—BuO—⟨phenyl⟩—Ala—Gly—(Cys)₂—Thr | Cys—[CH₂]—[CH₂]₂OH<br>  └—[CH₂]₆OH |
| B16 | n—BuO—⟨phenyl⟩—Ala—Gly—(Cys)₂—Thr | Cys—N⟨morpholine ring with O⟩ |
| B17 | n—BuO—⟨phenyl⟩—Ala—Gly—(Cys)₂—Thr | Cys—NH—CH⟨ring with O⟩ |

EXAMPLE 3

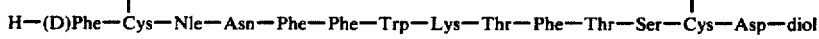

H—(D)Phe—Cys—Nle—Asn—Phe—Phe—Trp—Lys—Thr—Phe—Thr—Ser—Cys—Asp—diol

A solution of 1.15 g of Z-(D)Phe-Cys(MBzl)-Nle-Asn-Phe-Phe-Trp-Lys(Z)-Thr-Phe-Thr-Ser-Cys-(MBzl)-Asp-diol and 6 ml of thioanisole in 15 ml of trifluoroacetic acid is cooled to −10° C. and added to 12.5 ml of 2 molar boron-tris(trifluoroacetate) in trifluoroacetic acid. The mixture is stirred for 2 hours at −10° to −15° C. and 100 ml of cold (−70° C.) absolute methanol are added. The obtained solution is stirred with 2 l of absolute ether, and 10 ml of ~5 normal HCl in ether are added. The precipitated product is filtered off and washed with ether. The residue is immediately dissolved in 2.5 l dioxane/H₂O (7:3) and the solution adjusted to pH7 by the addition of 4 N NH₄OH. The solution is stirred in an open container at room temperature until it exhibits a negative reaction to tests for free-SH groups (e.g. using Ellmann-reagent). The solution is subsequently lowered to pH3-4 by the addition of HCl and the obtained solution concentrated under vacuum to approx. 500 ml. The concentrated solution is lyophilized and the lyophilization product purified by chromatography employing Bio-Gel P4 and 10% acetic acid as eluant. The fractions containing the desired product are combined and lyophilized, whereby the title compound is obtained: $[\alpha]_D^{20} = -51°$ (c=0.5 in 95% acetic acid). The starting material may be produced as follows:

(a) Z-Nle-Asn-Phe-Phe-OMe 11.8 g of Z-Asn-Phe-Phe-OMe are dissolved in 50 ml HBr/acetic acid (4 N) and allowed to stand for 1 hour at room temperature. Ether is added and the obtained precipitate filtered off, washed with ether and dried. The product is H-Asn-Phe-Phe-OMe.hydrobromide.

4.95 g of Z-Nle-OH dissolved in 50 ml tetrahydrofuran are cooled to −20° C. and 2.1 ml of N-methylmorpholine followed by 2.43 ml of chloroformic acid isobutylester are added to the solution with stirring. The solution is stirred for a further 10 minutes at −15° C. and a cold solution comprising 10.6 g of H-Asn-Phe-Phe-OMe. hydrobromide and 2.5 ml of N-methylmorpholine in 60 ml N,N-dimethylformamide/tetrahydrofuran (1:1) are added. The solution is stirred for 20 hours at 0° C. and for 2 hours at room temperature and subsequently stirred with aqueous ethanol. After filtration, washing with (a) methanol and (b) ether and drying, the title compound is obtained $[\alpha]_D^{20} = -31°$ (c=1.0 in dimethylformamide): decomposition at 235° C.

(b) BOC-Cys(MBzl)-Nle-Asn-Phe-Phe-OMe 15 g of Z-Nle-Asn-Phe-Phe-OMe in 300 ml dimethylformamide are hydrogenated using a 10% palladium on charcoal catalyst. The product is filtered over Hyflo, the filtrate stirred with ether and the precipitated product filtered off. After washing with ether and drying H-Nle-Asn-Phe-Phe-OMe is obtained.

10.6 g of BOC-Cys(MBzl)-ONP are added to a solution of 11.6 g of H-Nle-Asn-Phe-Phe-OMe in 150 ml dimethylformamide and the reaction mixture allowed to stand for ca. 20 hours at room temperature. Precipitation is effected employing methanol. The title compound is obtained after filtration, washing with (a), methanol and then (b) ether and drying: $[\alpha]_D^{20} = -30°$ (c=1.0 in dimethylformamide); decomposition at 230° C.

(c) Z-(D)Phe-Cys(MBzl)-Nle-Asn-Phe-Phe-OMe 10 g of BOC-Cys(MBzl)-Nle-Asn-Phe-Phe-OMe and 13.5 ml of thioanisole in 10 ml of CH₂Cl₂ are dissolved in 180 ml of trifluoroacetic acid and allowed to stand for 50 minutes at room temperature. Precipitation is effected by the addition of ether. After filtration, washing with ether and drying there is obtained H-Cys(MBzl)-Nle-Asn-Phe-Phe-OMe.trifluoroacetate.

7 g of the H-Cys(MBzl)-Nle-Asn-Phe-Phe-OMe.trifluoroacetate are dissolved in 90 ml of dimethylformamide and 1.1 ml triethylamine and 4.4 g Z-(D)Phe-ONP are added. The reaction mixture is allowed to stand for 20 hours. After precipitation employing a mixture of methanol and ether (2:1), filtration, washing with methanol/ether (2:1) and drying, the title compound is obtained: $[\alpha]_D^{20} = -21°$ (c = 1.0 in dimethylformamide); decomposition at 220° C.

(d) Z-(D)Phe-Cys(MBzl)-Nle-Asn-Phe-Phe-NHNH$_2$ 5 ml of hydrazine-hydrate are added to 5 g of Z-(D)Phe-Cys(MBzl)-Nle-Asn-Phe-Phe-OMe in 80 ml dimethylformamide and the mixture allowed to stand for 2 days at room temperature. The title compound is obtained after precipitation with methanol, filtration, washing with methanol and drying: $[\alpha]_D^{20} = -32°$ (c = 1.0 in dimethylformamide); decomposition at 248° C.

(e) H-Asp-diol 133 g of aspartic acid dimethyl ester.HCl in 75% ethanol are slowly added drop-wise with stirring at 5°-10° C. and under a nitrogen atmosphere to 126 g NaBH$_4$ in 650 ml of 75% ethanol. The reaction mixture is then stirred for ca. 20 hours at room temperature and for 2 hours at 35° C. The mixture is cooled and 250 ml of 50% acetic acid are slowly added drop-wise, followed by 2 N HCl until a pH of ~3 is reached. The solution is concentrated under vacuum and extracted with ether. The aqueous phase is adjusted to pH 9 by the addition of sodium carbonate and 1 N NaOH. The residue obtained after evaporation under vacuum is suspended in methanol, salts are precipitated by the addition of ether and filtered off and the filtrate is evaporated under vacuum. The title compound is obtained as a foam: $[\alpha]_D^{20} = +6.6°$ (c = 1.2 in 95% acetic acid).

(f) BOC-Cys(MBzl)-Asp-diol 3.8 ml of N-methylmorpholine and subsequently 4.4 ml of chloroformic acid isobutylester are added with stirring at −15° C. to a solution of 11.6 g of BOC-Cys(MBzl)-OH in 150 ml of tetrahydrofuran. After 15 minutes stirring at −15° C. a cold solution is added comprising 5 g of H-Asp-diol in a mixture of tetrahydrofuran and water and the siolution is stirred for 18 hours at 0°-5° C. The reaction mixture is then diluted with ethyl acetate and washed first with water and then with brine. The organic phase is dried over Na$_2$SO$_4$ and evaporated. The residue is purified chromatographically over Silica gel (CH$_2$Cl$_2$/MeOH 9:1). The title compound is obtained: $[\alpha]_D^{20} = -35°$ (c = 1.0 in methanol).

(g) H-Cys(MBzl)-Asp-diol.trifluoracetat 10 g of BOC-Cys(MBzl)-Asp-diol and 25 ml of anisole are added to 100 ml of trifluoroacetic acid at 0° C. and the mixture stirred for 1 hour at room temperature. Precipitation is effected employing a mixture of ether and petroleum ether. After decantation and drying the title compound is obtained as a resin: $[\alpha]_D^{20} = -15°$ (c = 1.0 in methanol).

(h) BOC-Lys(Z)-Thr-Phe-Thr-Ser-Cys(MBzl)-Asp-diol 6.6 ml HCl/ether (6 N) are added with stirring to a solution of 8.3 g of BOC-Lys(Z)-Thr-Phe-Thr-Ser-NHNH$_2$ in 200 ml dimethylformamide pre-cooled to −20° C., followed by a further 1.2 ml of tert.-butylnitrite. The solution is stirred for 10 minutes at −15° C., cooled to −25° C. and 5.6 ml of triethylamine are added followed by a cold solution of 5.2 g of H-Cys(MBzl)-Asp-diol.trifluoroacetate in 200 ml of dimethylformamide. A quantity of triethylamine corresponding to the amount of trifluoroacetate is then added and the mixture stirred for 3 hours at −5° C. and 18 hours at 0° C. The reaction mixture is filtered, washed with a little dimethylformamide and the filtrate is concentrated under vacuum. The solution is diluted with methanol and precipitation effected by the addition of water with stirring. After filtering off the precipitated product, washing with aqueous methanol and drying the title compound is obtained: $[\alpha]_D^{20} = -26°$ (c = 1.0 in dimethylformamide); m.p. 170° C. with decomposition.

(i) BOC-Trp-Lys(Z)-Thr-Phe-Thr-Ser-Cys(MBzl)-Asp-diol 1.15 g of BOC-Lys(Z)-Thr-Phe-Thr-Ser-Cys(MBzl)-Asp-diol are suspended in 2.5 ml of 50% acetic acid, cooled and added to 10 ml of trifluoroacetic acid. The yellowish solution is allowed to stand for 20 minutes at room temperature and is then stirred into 200 ml of ether. The precipitated product is filtered off, and washed with ether to yield H-Lys(Z)-Thr-Phe-Thr-Ser-Cys(MBzl)-Asp-diol.trifluoroacetate.

This product is then dissolved in 8 ml of dimethylformamide and 1.2 ml of N-methylmorpholine and 0.64 g of BOC-Trp-ONP are added. The mixture is allowed to stand overnight at room-temperature and is then stirred into approx. 100 ml of acetonitrile. The precipitated product is filtered off and washed with acetonitrile followed by ether. The residue is dissolved in a mixture of CH$_2$Cl$_2$/methanol added to acetonitrile and partially concentrated. The precipitated product is filtered off, washed with acetonitrile and ether and dried to yield the title compound: $[\alpha]_D^{20} = -26.5°$ (c = 1.1 in dimethylformamide).

(j) Z-(D)Phe-Cys(MBzl)-Nle-Asn-Phe-Phe-Trp-Lys(Z)-Thr-Phe-Thr-Ser-Cys-(MBzl)-Asp-diol 1.3 g of BOC-Trp-Lys(Z)-Thr-Phe-Thr-Ser-Cys(MBzl)-Asp-diol and 0.7 ml of β-mercaptoethanol are suspended in 10 ml CH$_2$Cl$_2$ and added to 40 ml of trfluoroacetic acid. The solution is allowed to stand for 30 minutes at room temperature. Concentrated under vacuum and precipitation effected with ether. After filtration, washing with ether and drying there is obtained H-Trp-Lys(Z)-Thr-Phe-Thr-Ser-Cys(MBzl)-Asp-diol. trifluoroacetate: $[\alpha]_D^{20} = -14°$ (c = 1.1 in 95% acetic acid).

1.06 g Z-(D)Phe-Cys(MBzl)-Nle-Asn-Phe-Phe-NHNH$_2$ are dissolved in 40 ml of dimethylformamide and cooled to −20° C. 0.7 ml of 5 N HCl in ether are then added with stirring followed by 1.20 ml of 10% tert. butylnitrite in dimethylformamide. The mixture is stirred for 15 minutes at −15° C., cooled to −25° C. and 0.5 ml of triethylamine are added. A cold solution of the H-Trp-Lys(Z)-Thr-Phe-Thr-Ser-Cys(MBzl)-Asp-diol. trifluoroacetate obtained as above in 8 ml of dimethylformamide is then added, followed by 0.15 ml triethylamine and the reaction mixture stirred for 16 hours at 0° C. and then for 2 hours at room temperature. The obtained mixture is stirred with a mixture of methanol/water (9:1), the precipitated product filtered off, washed with methanol and ether and dried to yield the title compound: $[\alpha]_D^{20} = -18.8°$ (c = 0.9 in dimethylformamide); decomposition from 200° C.

The peptides of formula I are useful as agents for the treatment of Diabetes Mellitus, acromegaly and angiopathy in view of their growth hormone secretion inhibitory activity in standard animal tests, e.g. as follows:

Male rats anaesthetized with Nembutal are administered with the peptide by injection in the jugular vein at several logarithmically staggered doses using at least 4 rats per dose. The rats are decapitated 15 minutes after administration and the blood collected. The growth hormone concentration in the blood serum is determined in conventional manner by radio immunoassay.

The peptides are administered in this test s.c. at a dose of from about 0.1 to about 500 µg/kg, for example, from about 0.5 to about 500 µg/kg animal body weight. For the compound of example 3 satisfactory results are obtained at a dose of from about 0.1 to 100 µg/kg.

In addition to the foregoing it has also been found that the compound of example 3 has the additional advantageous characteristic of not influencing insulin-secretion even at higher doses. This permits its use in the treatment of patients with their own insulin secretion without recourse to substitution therapy. The influence on insulin secretion may for example be demonstrated by the following test method:

Normally fed male rats weighing from 200–250 g are subjected to Nembutal narcosis. 45 minutes later the compound of example 3 is administered i.v. in logarithmically staggered doses employing at least 3 rats per dose. 10 minutes later 0.5 g/kg of glucose is injected i.v. and after a further 5 minutes the rats are decapitated and the blood collected. The determination of the insulin level in the bloodserum is carried out by radio immunoassay. When tested at levels sufficient to effect growth hormone secretion and rising to doses of several Mg/kg, the compound exhibited no influence on insulin secretion.

For the growth hormone secretion inhibitory use the dosage will, of course, vary depending on the compound employed, mode of administration and therapy desired. However, in general, satisfactory results are obtained when administered at a daily dosage of from 0.5 to about 1000 µg/kg animal body weight, conveniently given in divided doses 2 to 4 times a day or in sustained release form. For the larger mammal, the total daily dosage is in the range of from 0.07 to about 70 mg, and unit dosage forms, e.g. suitable for parenteral administration comprise from about 0.02 to about 35 mg of the compound admixed with a solid or diluent.

In the specific case of the compound of example 3 satisfactory growth hormone secretion inhibition is achieved employing a dosage of from about 1.0 to about 100 µg/kg. Suitable daily dosages for larger mammals are in this case in the range of from about 0.07 to about 7 mg with unit dosage forms comprising from about 0.02 to about 3.5 mg of the compound admixed with a solid or liquid diluent.

The compounds of Examples A29, A47 and A48 exhibit especially interesting activity.

The compounds of formula I may be administered in pharmaceutically acceptable acid addition salt or complex form. Such acid addition salt or complex forms exhibit the same order of activity as the free base forms and are readily prepared in conventional manner. The present invention also provides a pharmaceutical composition comprising a compound of formula I, in free base form, in complex form, or in pharmaceutically acceptable acid addition salt form, in association with a pharmaceutical carrier or diluent. Such compositions may be in the form of, for example, a tablet or a solution for injection or infusion, buffered e.g. at from pH 5 to 8.

The present invention also comprises pharmaceutical preparations containing compounds of formula I, wherein $R_1$ is H—(α-amino)—isobutyryl—NH— or H—(D)—Ala—NH, X is Lys, Y is Asn, Z is —$CONR_4R_5$ or —CO—N $(CH_2)_4$ or 5. Each B preferably signifies hydrogen.

One series of compound groups may be individually formulated as follows:
In one group of compounds $R_1$ is significance (i).
In another group of compounds $R_1$ is significance (ii).
In another group of compounds $R_1$ is significance (iii).
In another group of compounds $R_1$ is significance (iv).
In another group of compounds $R_1$ is significance (v).
In another group of compounds $R_1$ is significance (vi).
In another group of compound $R_1$ is significance (vii).
In another group of compounds $R_1$ is significance (viii).
In another group of compounds $R_1$ is significance (ix).
In another group of compounds $R_1$ is significance (x).

A second series of compound groups may be individually formulated as follows:
In a group of compounds Z is significance (i).
In another group of compounds Z is significance (ii).
In another group of compounds Z is significance (iii).
In another group of compounds Z is significance (iv).
In another group of compounds Z is significance (v).
In another group of compounds Z is significance (vi).
In another group of compounds Z is significance (vii).
In another group of compounds Z is significance (viii).
In another group of compounds Z is significance (ix).
In another group of compounds Z is significance (x).
In another group of compounds Z is significance (xi).
In another group of compounds Z is significance (xii).

In another group of compounds Q is CysAsparaginol.

When $R_1$ has the significance (xii), $R_6$ can be a 5- or 6-membered saturated heterocycle the sole hetero-atom of which is oxygen i.e. $R_6$ is tetrahydrofuryl or tetrahydropyranyl. $R_6$ can also be a 5- or 6-membered lactone ring. The peptide sequence may contain at least one unit in D form. For example X may be D-Lys, D-Nle or D-Cys. Y may be D-Asn, D-Glu or D-Thr. Z may, for example, be —CO— D—asparaginol, —CO— D—leucinol, —CO— D—isoleucinol, —CO— D—valinol, —CO— D—norleucinol, —CO— D—glutaminol, —CO— D—threoninol, —CO— D—Ser and the corresponding amides thereof. Other members of the peptide sequence may be —D—Phe—, —D—Trp—, D—Lys—, —D—Thr—, —D—Ser—. The significance —D—Trp—, is preferably in position 8. The significance —D—Cys—, is preferably in position 14.

It will be appreciated that further groups are formulated by combining individually any group from the first series with a group from the second series. Additionally, the preferences indicated throughout the specification may be applied individually to restrict the scope of any of these groups.

What we claim is:
1. A compound of formula I,

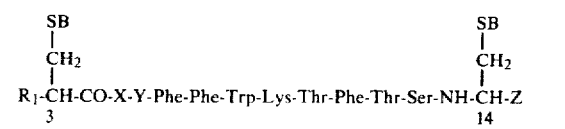

wherein $R_1$ is (i) H,
(ii) NH₂,
(iii) H—Ala—NH—; H—Tyr—NH—; H—Cys—NH—; H—Val—NH—; H—Lys—NH—; H—(α-amino-isobutyryl)—NH—; H—Phe—NH
(iv) NH₂—NH—CO—NH—;
(v) C₆H₅.NH—CO—Gly—NH—; H—Ala—Gly—NH—; H—Val—Gly—NH—; H—α—phenyl—Gly—NH—,
(vi) R₂—A—CO—NH—,
wherein
R₂ is lower alkyl, phenyl, or phenyl substituted by halogen, hydroxy, amino lower alkyl or lower alkoxy,
A is a direct bond, alkylene containing up to 6 carbon atoms or —NH—,
(vii) R₂—Ala—NH—; R₂—Ala—Gly—NH—; wherein R₂ is as defined above,
(viii) C₆H₅.A$^I$.CO—M—NH—,
wherein
A$^I$ is an alkylene chain of up to 6 carbon atoms, and —M— is —(mono- or di-Hal)—Phe, —Gly— or —Ala—,
(ix) T—(mono- or di-Hal)—Phe—NH, wherein T— is H—, H—Val— or benzoyl—,
(x)

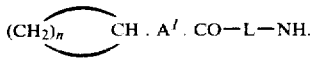

(CH₂)$_n$  CH . A$^I$ . CO—L—NH.

wherein
A$^I$ is as defined above, and
—L— is —Val—(mono- or di-Hal)— Phe—α—phenyl—Gly—, and
n is an integer between 4 and 10,
each B is hydrogen or the two radicals B form a direct bond,
X is —Lys—, or —Nle—, and
Y is —Asn—, —Gln— or —Thr—, and
Z signifies the radicals:
(i) —CO—asparaginol; —CO—leucinol; —CO—iso-leucinol; —CO—valinol; —CO—norleucinol; —CO—glutaminol; —CO—threoninol;
(ii) —CO—Leu; —CO—Ser; —CO—Iso—Leu; —CO—Val, and their corresponding amides, wherein the amide portion signifies the radical —CO—NR₄R₅ (wherein R₄ and R₅ independently are hydrogen or lower alkyl) or the radical

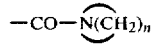

—CO—N(CH₂)$_n$ (wherein n is as defined above);
(iii) —CO—ThrOR₃ or —CO—SerOR₃ (wherein R₃ is lower alkyl); or
(iv) —CO—NH—(CH₂)$_k$—OH (wherein k is an integer between 2 and 6), or

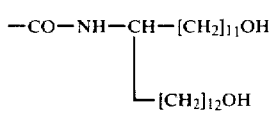

—CO—NH—CH—[CH₂]$_{l_1}$OH
           |
           [CH₂]$_{l_2}$OH (wherein l₁ and l₂ independently signify a whole number from 1 to 6); wherein in formula I the unit containing radicals R₁, X, Y and Z, as well as in the remaining units of the peptide sequence, at least one unit may be present in D form, with the proviso that when R₁ is H—Cys—NH or H—(D)—Cys—NH, B—B is other than a direct bond, or a pharmaceutically acceptable acid addition salt or complex thereof.

2. A compound of claim 1 wherein
Z signifies the radicals
(ii) —CO—Asparaginol; —CO—leucinol; —CO—iso-leucinol; —CO—valinol; —CO—norleucinol; —CO—glutaminol; —CO—threoninol; or
(v) —CO—NH—(CH₂)$_k$—OH (wherein k is an integer between 2 and 6), or

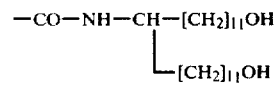

—CO—NH—CH—[CH₂]$_{l_1}$OH
           |
           [CH₂]$_{l_1}$OH wherein l₁ and l₂ independently signify a whole number from 1 to 6).

3. A compound of claim 2 wherein Z represents

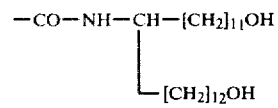

—CO—NH—CH—[CH₂]$_{l_1}$OH
           |
           [CH₂]$_{l_2}$OH (wherein l₁ and l₂ independently signify a whole number from 1 to 6).

4. A compound of formula I of claim 1 of the formula

P-Phe-Phe-Trp-Lys-Thr-Phe-Thr-Ser-Q wherein
(a) P represents H-(4Cl)Phe-Cys-Nle-Asn, and Q represents Cys-Asparaginol;
(b) P represents H-Iabu-Cys-Nle-Asn, and Q represents Cys-Asparaginol;
(c) P represents H-Iabu-Cys-Lys-Asn, and Q represents Cys-Asparaginol;
(d) P represents H-(D)-Ala-Gly-Cys-Lys-Asn, and Q represents Cys-Asparaginol;
(e) P represents H-(D)-Ala-Gly-Cys-Nle-Asn, and Q represents Cys-Asparaginol;
(f) P represents H-(3Cl)Phe-Cys-Nle-Asn, and Q represents Cys-Asparaginol;
(g) P represents H-(2Cl)Phe-Cys-Nle-Asn, and Q represents Cys-Asparaginol;
(h) P represents H-(3,4diCl)Phe-Cys-Nle-Asn, and Q represents Cys-Asparaginol;
(i) P represents h-(4Cl)Phe-Cys-Nle-Asn, and Q represents Cys-NH-[CH₂]₂-OH;
(j) P represents H-(4Cl)Phe-Cys-Nle-Asn, and Q represents Cys-NH-[CH₂]₃-OH;
(k) P represents H-(4Cl)Phe-Cys-Nle-Asn, and Q represents Cys-Threoninol;
(l) P represents H-(4Cl)Phe-Cys-Nle-Asn, and Q represents

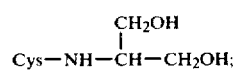

CH₂OH
           |
Cys—NH—CH—CH₂OH;

(m) P represents H-(4Cl)Phe-Cys-Nle-Asn, and Q represents Cys-Glutaminol;
(n) P represents H-(4Cl)Phe-Cys-Nle-Asn, and Q represents (o) P represents H-(4Cl)Phe-Cys-Nle-Asn, and Q represents

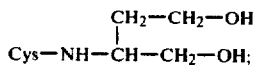

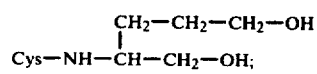

(p) P represents H-(D)-Phe-Cys-Nle-Asn, and Q represents Cys-Asparaginol;
(q) P represents H-(D)-Val-(4Cl)Phe-Cys-Nle-Asn, and Q represents Cys-Asparaginol; and
(r) P represents H-(D)-Ala-(4Cl)Phe-Cys-Nle-Asn, and Q represents Cys-Asparaginol, and corresponding cyclic compounds, wherein each B of compounds of Formula I in claim 1 are bridged to each other, or a pharmaceutically acceptable acid addition salt or complex thereof.

5. A compound of formula

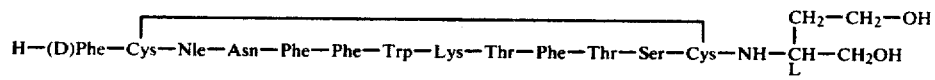

6. A pharmaceutical composition useful in inhibiting growth hormone secretion comprising as active ingredient a pharmaceutically effective amount of a compound of formula I as defined in claim 1.

7. A method of inhibiting growth hormone secretion in a subject in need of such treatment, which method comprises administering an effective amount of a compound of formula I as defined in claim 1.

* * * * *